United States Patent
Matsunaga

(10) Patent No.: US 11,769,255 B2
(45) Date of Patent: Sep. 26, 2023

(54) DIAGNOSIS ASSISTING DEVICE, AND IMAGE PROCESSING METHOD IN DIAGNOSIS ASSISTING DEVICE

(71) Applicant: CASIO COMPUTER CO., LTD., Tokyo (JP)

(72) Inventor: Kazuhisa Matsunaga, Fussa (JP)

(73) Assignee: CASIO COMPUTER CO., LTD., Tokyo (JP)

(*) Notice: Subject to any disclaimer, the term of this patent is extended or adjusted under 35 U.S.C. 154(b) by 0 days.

(21) Appl. No.: 17/747,327

(22) Filed: May 18, 2022

(65) Prior Publication Data
US 2022/0277429 A1  Sep. 1, 2022

Related U.S. Application Data

(62) Division of application No. 15/642,280, filed on Jul. 5, 2017, now Pat. No. 11,379,958.

(30) Foreign Application Priority Data

Sep. 2, 2016 (JP) .................................. 2016-171595
Apr. 17, 2017 (JP) .................................. 2017-081594

(51) Int. Cl.
G06T 7/00 (2017.01)
A61B 5/00 (2006.01)
(Continued)

(52) U.S. Cl.
CPC ............ G06T 7/0012 (2013.01); A61B 5/444 (2013.01); A61B 5/7264 (2013.01); G06T 5/002 (2013.01);
(Continued)

(58) Field of Classification Search
CPC .................. A61B 5/444; A61B 5/7264; G06T 2207/10024; G06T 2207/30088;
(Continued)

(56) References Cited

U.S. PATENT DOCUMENTS 5,594,807 A * 1/1997 Liu ........................... G06T 5/40
                                              382/128
6,108,037 A  8/2000 Takei
(Continued)

FOREIGN PATENT DOCUMENTS

CN  1898945 A  1/2007
CN  105761260   7/2016
(Continued)

OTHER PUBLICATIONS

J. Kawahara, A. BenTaieb and G. Hamarneh, "Deep features to classify skin lesions," 2016 IEEE 13th International Symposium on Biomedical Imaging (ISBI), 2016, pp. 1397-1400, doi: 10.1109/ISBI.2016.7493528. (Year: 2016).*
(Continued)

Primary Examiner — Boniface Ngathi
Assistant Examiner — Milton Truong
(74) Attorney, Agent, or Firm — Holtz, Holtz & Volek PC

(57) ABSTRACT

An image processing method in a diagnosis assisting device that diagnoses lesions from a picked-up image, the method including A) performing an image correction on the picked-up image for diagnosis, and B) obtaining an input image to an identifier that identifies diseases based on the picked-up image having undergone the image correction. In A), when a brightness correction is performed as the image correction, a peripheral area other than a diagnosis area that has a high probability as diseases in the picked-up image is set to be a measuring area, a brightness histogram is created relative to the measuring area, a correction gain value is calculated based on a peak value of the created brightness histogram, and each of pixels in a color space is corrected by using the calculated correction gain value.

5 Claims, 14 Drawing Sheets

(51) Int. Cl.

| | |
|---|---|
| *G06T 5/40* | (2006.01) |
| *G06T 7/11* | (2017.01) |
| *G06V 10/56* | (2022.01) |
| *G06V 20/69* | (2022.01) |
| *G06T 5/00* | (2006.01) |
| *H04N 1/60* | (2006.01) |
| *H04N 1/62* | (2006.01) |

(52) U.S. Cl.
CPC .............. *G06T 5/009* (2013.01); *G06T 5/40* (2013.01); *G06T 7/11* (2017.01); *G06V 10/56* (2022.01); *G06V 20/695* (2022.01); *G06T 2207/10024* (2013.01); *G06T 2207/20081* (2013.01); *G06T 2207/20084* (2013.01); *G06T 2207/30088* (2013.01); *G06T 2207/30096* (2013.01); *H04N 1/6005* (2013.01); *H04N 1/6027* (2013.01); *H04N 1/628* (2013.01)

(58) Field of Classification Search
CPC ............. G06T 2207/30096; G06T 5/40; G06T 7/0012; G06T 7/11; H04N 1/6005; H04N 1/6027; G06V 10/50; G06V 20/695
See application file for complete search history.

(56) References Cited

U.S. PATENT DOCUMENTS

| | | | |
|---|---|---|---|
| 6,141,437 | A | 10/2000 | Xu et al. |
| 7,486,836 | B2 | 2/2009 | Kato |
| 10,362,984 | B2 | 7/2019 | Adiri et al. |
| 10,586,331 | B2 | 3/2020 | Matsunaga |
| 2005/0100208 | A1 | 5/2005 | Suzuki et al. |
| 2006/0023273 | A1* | 2/2006 | Kato .................. H04N 1/4074 358/521 |
| 2007/0248282 | A1 | 10/2007 | Suzuki |
| 2007/0273793 | A1 | 11/2007 | Harada et al. |
| 2008/0260218 | A1 | 10/2008 | Smith et al. |
| 2009/0295941 | A1* | 12/2009 | Nakajima ................. G06T 5/50 348/229.1 |
| 2010/0265356 | A1 | 10/2010 | Takano et al. |
| 2015/0025343 | A1 | 1/2015 | Gareau et al. |
| 2016/0100148 | A1 | 4/2016 | Paliy |
| 2016/0275681 | A1* | 9/2016 | D'Alessandro ...... A61B 5/7425 |
| 2018/0008188 | A1* | 1/2018 | Adiri .................. A61B 5/0077 |
| 2018/0228426 | A1 | 8/2018 | Sinai et al. |
| 2019/0290187 | A1 | 9/2019 | Ari et al. |

FOREIGN PATENT DOCUMENTS

| | | |
|---|---|---|
| EP | 3291174 A1 | 3/2018 |
| JP | 2006325015 A | 11/2006 |
| WO | 2013119102 A1 | 8/2013 |
| WO | 2015137542 A1 | 9/2015 |
| WO | 2016120862 A1 | 8/2016 |

OTHER PUBLICATIONS

Australian Office Action dated Aug. 30, 2019 issued in Australian Patent Application No. 2018282455.

Australian Office Action dated Jan. 9, 2019 issued in counterpart Australian Application No. 2017213456.

Catarina Barata, et al., "Improving Dermoscopy Image Analysis Using Color Constancy," 5 Pages http://vislab.isr.ist.utl.pt/wp-content/uploads/2012/12/14-ICIPa.pdf.

Chinese Office Action (and English translation thereof) dated Jan. 16, 2020, issued in counterpart Chinese Application No. 201710610609.4.

Chinese Office Action (and English translation thereof) dated May 6, 2020 issued in counterpart Chinese Application No. 201710610609.4.

European Office Action dated Dec. 17, 2021, issued in European Application No. 17179753.3.

European Office Action dated May 12, 2020 issued in counterpart European Application No. 17179753.3.

Extended European Search Report (EESR) dated Oct. 27, 2017 issued in counterpart European Application No. 17179753.3.

Japanese Office Action dated Jan. 9, 2018 issued in counterpart Japanese Application No. 2017-081594.

Notice of Allowance dated Mar. 22, 2022, issued in parent U.S. Appl. No. 15/642,280.

Office Action (Final Rejection) dated Sep. 28, 2020, issued in parent U.S. Appl. No. 15/642,280.

Office Action (Non-Final Rejection) dated Aug. 18, 2021, issued in parent U.S. Appl. No. 15/642,280.

Office Action (Non-Final Rejection) dated Mar. 20, 2020, issued in parent U.S. Appl. No. 15/642,280.

Barata, et al., "Improving Dermoscopy Image Classification Using Color Constancy", IEEE Journal of Biomedical and Heal th Informatics, vol. 19, No. 3, May 2015, pp. 1146-1152.

Ercal, et al., "Neural Network Diagnosis of Malignant Melanoma From Color Images", IEEE Transactions on Biomedical Engineering, IEEE, USA, vol. 41, No. 9, Sep. 1994, pp. 837-845.

Kawahara, et al., "Deep features to classify skin lesions", 2016 IEEE 13th International Symposium on Biomedical Imaging (ISBI), Prague, 2016, pp. 1397-1400.

Messadi, et al., "Extraction of specific parameters for skin tumour classification", Journal of Medical Engineering & Technology, vol. 33, No. 4, May 2009, pp. 288-295.

\* cited by examiner

1 : DIAGNOSIS ASSISTING DEVICE

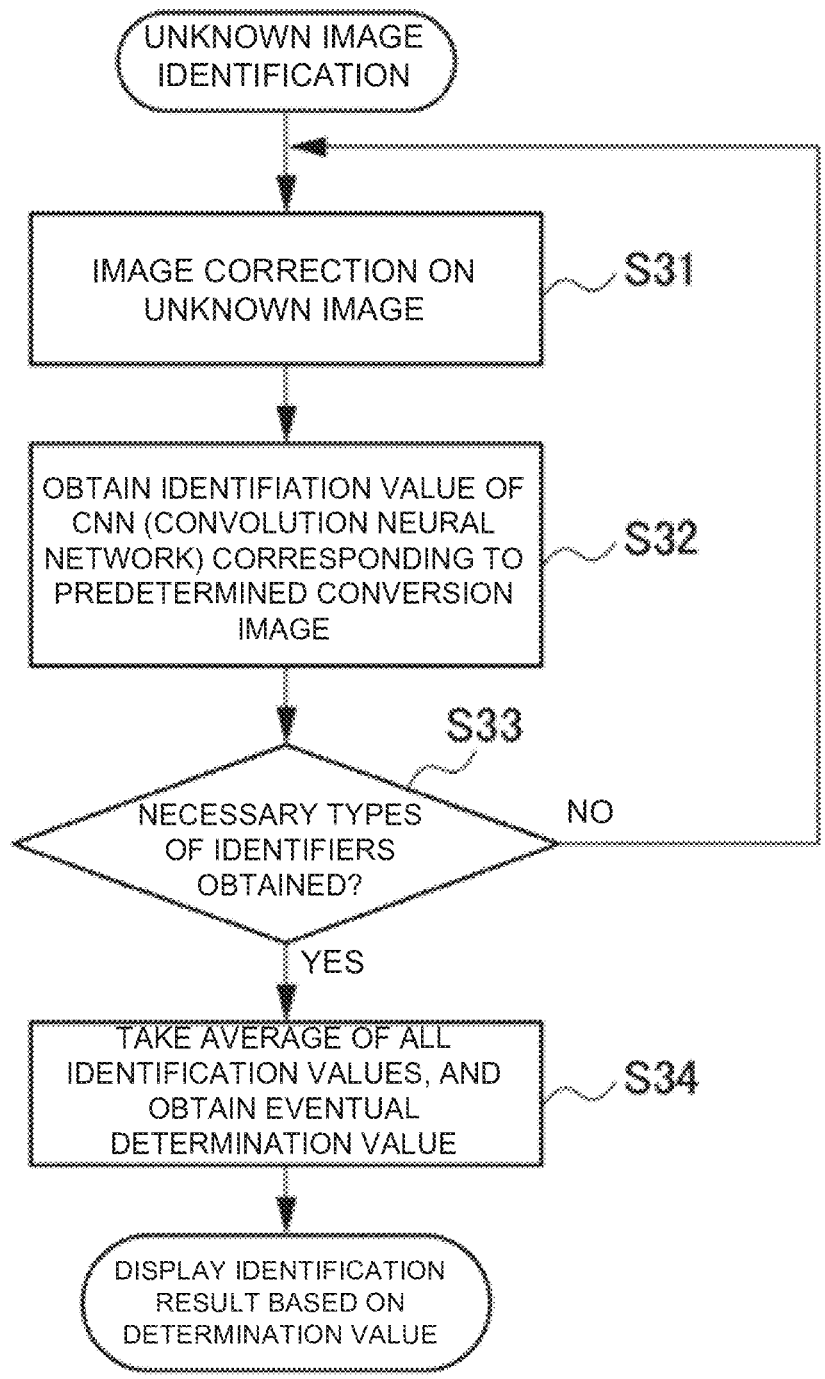

DIAGNOSIS ASSISTING DEVICE, AND IMAGE PROCESSING METHOD IN DIAGNOSIS ASSISTING DEVICE

CROSS-REFERENCE TO RELATED APPLICATION

This application is a Divisional Application of U.S. application Ser. No. 15/642,280, filed on Jul. 5, 2017, which claims the benefit of Japanese Patent Application No. 2016-171595, filed on Sep. 2, 2016, and Japanese Patent Application No. 2017-081594, filed on Apr. 17, 2017, the entire disclosures of all of which are incorporated by reference herein.

FIELD

This application relates generally to a diagnosis assisting device, and an image processing method in the diagnosis assisting device.

BACKGROUND

Visual check is always carried out for skin lesions, and a medical doctor is capable of obtaining a large quantity of information by visual check. When, however, the visual check is carried out by bare eye or magnifier only, even a distinction between a mole and a fleck is difficult, and a differential diagnosis between a benign tumor and a malignant tumor is also difficult. Hence, dermoscopy diagnosis of picking up an image of lesions using a camera provided with a dermoscope is carried out.

When, however, the color shade of a skin color part of a non-affected area and the brightness thereof differ, a medical doctor focuses on only the difference when attempting to obtain an observation by visual check, disrupting the medical doctor from properly grasping the difference of the affected area.

Hence, as disclosed in Non Patent Literature 1, the color is corrected, or as disclosed in Patent Literature 1, the brightness is corrected.
Non Patent Literature 1: IMPROVING DERMOSCOPY IMAGE ANALYSIS USING COLOR CONSTANCY (http://vislab.isr.ist.utl.pt/wp-content/uploads/2012/12/14-ICIPa.pdf) (Browsed on May 5, 2016)
Patent Literature 1: Unexamined Japanese Patent Application Kokai Publication No. 2006-325015

SUMMARY

In order to accomplish the above objective, according to an aspect of the present disclosure, an image processing method in a diagnosis assisting device that diagnoses lesions from a picked-up image includes:

(A) performing an image correction on the picked-up image for diagnosis, in which in the (A), a peripheral area other than a diagnosis area that has a high probability as diseases in the picked-up image is set to be a measuring area when an image correction is performed.

Other features of the present disclosure will become more apparent by the descriptions and the accompanying figures.

BRIEF DESCRIPTION OF THE DRAWINGS

A more complete understanding of this application can be obtained when the following detailed description is considered in conjunction with the following drawings, in which:

FIG. 18 is a flowchart illustrating a flow of a diagnosis image identifying (unknown image identifying) process according to Embodiment 3.

DETAILED DESCRIPTION

Figure 1:
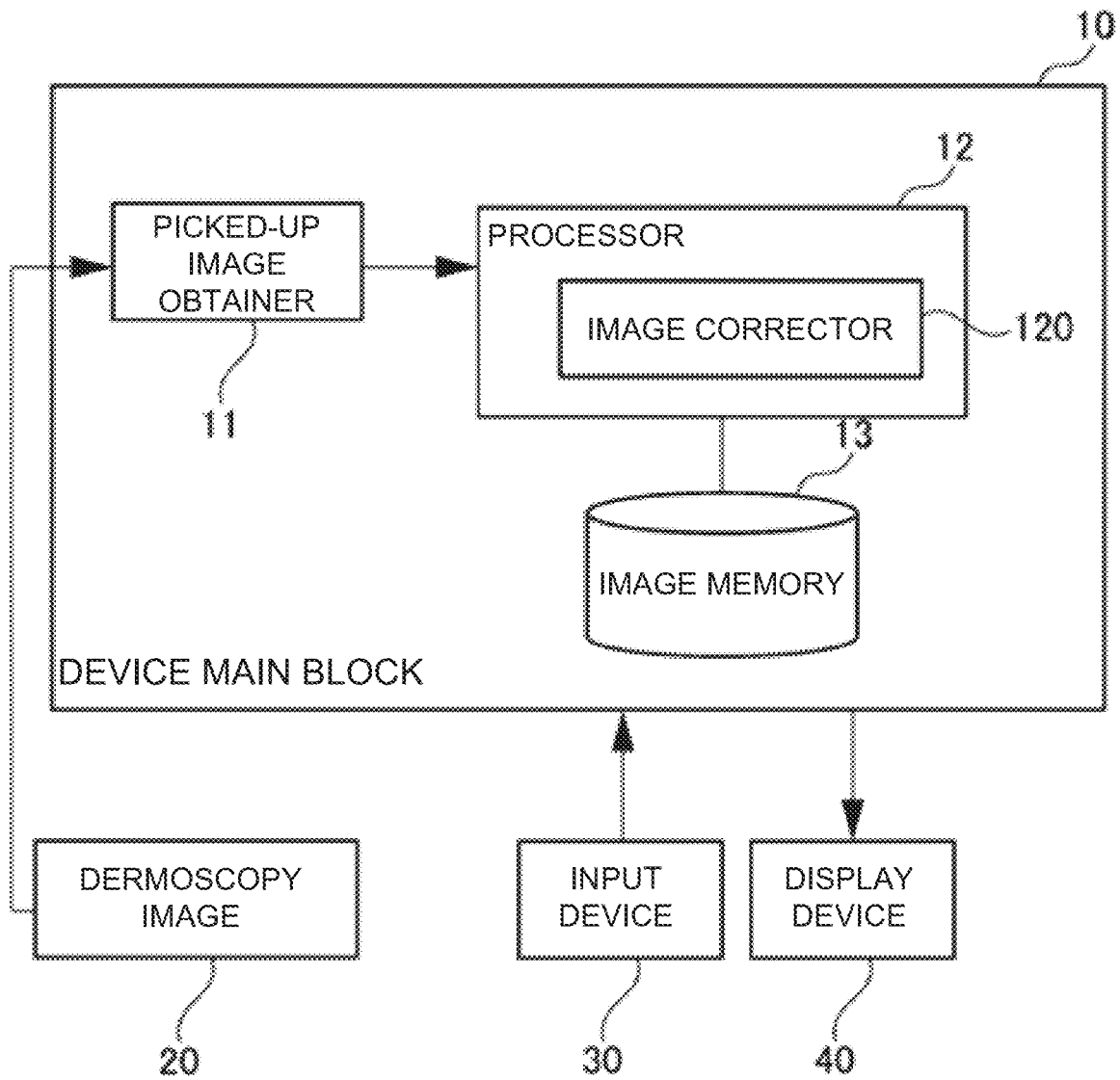
FIG. 1 is a block diagram illustrating a structure of the diagnosis assisting device according to an embodiment of the present disclosure.

Embodiments to carry out the present disclosure (hereinafter, referred to as embodiments) will be described in detail with reference to the accompanying figures. In the following figures, the same reference numeral or sign will be given to the same component through the entire description of the embodiments.

Structure According to Embodiment

FIG. 1 is a block diagram illustrating a structure of a diagnosis assisting device 1 according to an embodiment. As illustrated in FIG. 1, the diagnosis assisting device 1 according to this embodiment is connected to an imaging device 20 with a dermoscope (dermoscopy imaging device 20).

The dermoscopy imaging device 20 picks up an image in accordance with an instruction from a device main block 10 of the diagnosis assisting device 1, stores a dermoscopy image that is the picked-up image in an image memory 13, and displays this image on a display device 40. In addition, the picked-up image is subjected to an image processing by the device main block 10, stored in the image memory 13, and displayed on the display device 40.

An input device 30 is utilized to instruct a start of the image pickup of the dermoscopy image, select the part in the dermoscopy image to be described later. The display device 40 includes, for example, a liquid crystal display (LCD) monitor, and the input device 30 includes, for example, a mouse.

The device main block 10 includes a picked-up image obtainer 11, a processor 12, and the image memory 13.

The picked-up image obtainer 11 captures the picked-up image by the dermoscopy imaging device 20, and outputs the image to the processor 12. The processor 12 sets, as a measuring area, a peripheral part (also referred to as a peripheral area in the following) other than the center part (also referred to as a diagnosis area in the following) that has a high probability of diseases in the dermoscopy image (picked-up image). For this purpose, the processor 12 includes an image corrector 120.

The image corrector 120 performs an image correction that is either a color correction to correct the color shade or a brightness correction. When performing the color correction, the image corrector 120 sets the peripheral part other than the center part that has a high probability of diseases in the picked-up image as the measuring area, and sets a correction conversion target to be a skin color, thereby performing a color correcting process. Conversely, when performing a brightness correction, the image corrector 120 sets the peripheral part other than the center part that has a high probability of diseases in the picked-up image as the measuring area, creates a brightness histogram relative to the measuring area, calculates a correction gain value based on the peak value of the brightness histogram, and multiplies each of R, G, and B by the same correction gain value so as not to change the color phase, thereby obtaining a corrected brightness value. In this embodiment, the description will be given of an example case in which the color space is an RGB color space, but this embodiment is also applicable to, for example, a YUV color space, an HSV color space, and the like.

The image memory 13 stores, in addition to the dermoscopy image of an affected area picked up by the dermoscopy imaging device 20, various data such as an image created during the execution of a program to be described later. The image memory 13 includes semiconductor, magnetic, optical memory elements, and the like.

A case in which the image corrector 120 performs the image correction that is the color correction will be described as Embodiment 1, while a case in which the image corrector 120 performs the brightness correction will be described as Embodiment 2 below.

Structure According to First Embodiment

Figure 2:
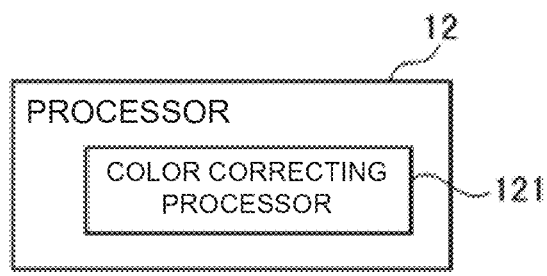
FIG. 2 is a block diagram illustrating a structure of a processor according to Embodiment 1.

As illustrated in FIG. 2, the processor 12 according to Embodiment 1 includes a color correcting processor 121. The color correcting processor 121 sets the peripheral part other than the center part that has a high probability of diseases in the picked-up image in order to perform the color correction, and sets the correction conversion target as a skin color, thereby performing the color correcting process. In this case, the color correcting processor 121 sets the center part as a center circle of the picked-up image, obtains, as for each of R, G, and B, an Lp norm of the corresponding pixel within the measuring area other than the center circle, normalizes by a coefficient k in such a way that the L2 norms of $e_R$, $e_G$ and $e_B$ becomes 1, a color gain is set using a product of ec times the square root of 3, and multiplies each original pixel value $I_R$, $I_G$, and $I_B$ of R, G, and B pixels by the corresponding gain coefficient of R, G, B, thereby performing the color correcting process of the original image.

The color correcting processor 121 may set a limiter to the corrected pixel value at the time of correction and conversion when a skin color assumption is not satisfied such that the entire plane is blood color in the measuring area.

Actions According to First Embodiment

A color correcting process action by the processor 12 (color correcting processor 121) according to Embodiment 1 will be described in detail with reference to the flowchart that is FIG. 3.

Under an instruction given by a medical doctor through the input device 30, first, when the dermoscopy imaging device 20 picks up an image of an affected area, the device main block 10 causes the picked-up image obtainer 11 to capture the picked-up dermoscopy image subjected to correction (step S301), and to output the captured image to the processor 12.

Figure 4:
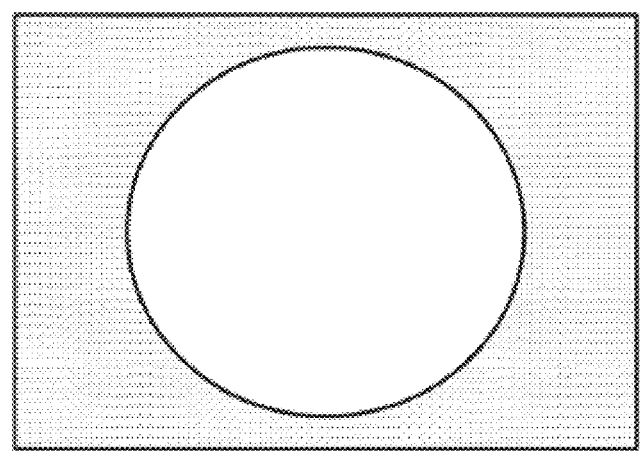
FIG. 4 is a diagram cited to describe a color information measuring area according to Embodiment 1.

In response to the output image, the processor 12 sets a color information measuring area (step S302). More specifically, for example, as illustrated in FIG. 4, the image corrector 120 sets, as an obtainment area, an area other than the image center circle (that is, the peripheral part other than the center part) in order to obtain the color shade of the image. This is to make a determination on the color shade of the image based on the skin color, and to avoid the affected area that is the image center part that has the color changed variously.

Next, the color correcting processor 121 calculates a color norm sum based on the following arithmetic expressions (1), (2) and (3) for each color within the color information measuring area (step S303).

[Formula 1]

$$\left(\frac{\int (I_c\{x\})^p dx}{\int dx}\right)^{1/p} = ke_c \quad (1)$$

$$c \in \{R, G, B\} \quad (2)$$

$$\sqrt{e_R^2 + e_G^2 + e_B^2} = 1 \quad (3)$$

That is, the color correcting processor 121 obtains, as for each R, G, and B pixel within the color information measuring area set in the step S302, the Lp norm (however, calculation is made as p=6) of the corresponding pixel, and normalizes by the coefficient k in such a way that the L2 norms of $e_R$, $e_G$ and $e_B$ become 1 (arithmetic expression (3)). The integral ∫ in the arithmetic expression (1) means integration to all areas. In arithmetic expression (1), IC represents the original pixel value of a given one of the R, G, and B pixels, as indicated by arithmetic expression (2).

Next, the color correcting processor 121 calculates color correction gains ($d_R$, $d_G$ and $d_B$) in accordance with the following arithmetic expressions (4) and (5) (step S304).

[Formula 2]

$$d_c = \frac{1}{\sqrt{3} \, e_c} \quad (4)$$

-continued $$\begin{pmatrix} I'_R \\ I'_G \\ I'_B \end{pmatrix} = \begin{pmatrix} d_R & 0 & 0 \\ 0 & d_G & 0 \\ 0 & 0 & d_B \end{pmatrix} \begin{pmatrix} I_R \\ I_G \\ I_B \end{pmatrix} \quad (5)$$

That is, the color correcting processor 121 calculates a product of ec times the square root of 3 (arithmetic expression (4)), thereby setting the color gain in accordance with a color reproduction matrix (arithmetic expression (5)). In arithmetic expression (5), IR, IG, and IB represent the original pixel values of the corresponding R, G, and B pixels.

When the original image substantially indicates R only, since an R value $I'_R$ is excessively reduced, the color correcting processor 121 needs to set a limiter so as not to decrease the R value below the setting minimum value (step S305).

Next, the color correcting processor 121 performs a gain balance adjustment relative to the correction target (step S306). That is, in the case of a normal white balance correction, the entire balance is accomplished based on gray world assumption, but in the case of the dermoscopy image subjected to correction, the skin color is dominant, and thus the skin color changes to a blue-green color when adjusted based on the gray world assumption. Hence, the conversion target is set in accordance with the following arithmetic expressions (6), (7), and (8). That is, the color shade of the conversion target is set in accordance with the specific skin color.

[Formula 3]

$$d_{R2}=d_R*1.0 \quad (6)$$

$$d_{G2}=d_G*0.9 \quad (7)$$

$$d_{B2}=d_B*1.0 \quad (8)$$

That is, the color correcting processor 121 executes an adjustment of the gain coefficient in such a way that the total ratio of R, G, and B norms becomes 1.0:0.9:1.0 so as to express the difference in color shade by the conversion target as color contrast. For example, as for the color shade of the dermoscopy image subjected to correction, the total ratio of the R, G, and B norms is set to be 1.0:1.0:1.0 to express the color shade of the conversion target image, or the total ratio of R, G, and B norms is set to be 1.0:0.9:1.0 as executed in step S306 to adjust the gain, thereby expressing the color shade of the conversion target image.

Next, the color correcting processor 121 multiplies the respective R, G, and B pixels by the R, G, and B gain coefficients obtained in the step S306 to perform the color correcting process on the dermoscopy image that is the original image (step S307), and ends the sequential color correcting process.

Effects of First Embodiment

According to the diagnosis assisting device 1 of Embodiment 1, the processor 12 (color correcting processor 121) sets, as the color information measuring area, the peripheral part other than the center part that has a high probability of the affected area when correcting the color shade (color correction) of the dermoscopy image subjected to correction, and sets the correction target to be a skin color, thereby performing a natural and robust correction. In addition, in the case the image that is entirely a blood color that does not satisfy the skin color assumption, by setting the limiter at the time of correction, an unnatural correction can be suppressed. Hence, a pre-process to classify the image by eliminating an adverse effect of the imaging light source and that of individual difference of melanin concentration, and the like, and an image presentation are enabled. This facilitates a user to, in particular, overview and grasp a difference of the affected area when multiple images are presented side by side. Consequently, a highly precise diagnosis assistance is enabled. The diagnosis assisting device 1 may present the image one by one for comparison (the same is true of the following descriptions).

According to the diagnosis assisting device 1 of this embodiment, the description has been given of a case in which the picked-up image that has the RGB color space is to be corrected, but the present disclosure is not limited to the RGB space, and the color correction can be made according to the present invention on the picked-up image that has a YUV color space expressed using a brightness signal Y and two color difference signals U and V, or an HSV color space expressed by a color phase H, a colorfulness S, and a brightness V, or the like. In the case of the YUV color space, the respective Y, U, and V pixels are multiplied by the same correction gain value, and in the case of the HSV color space, the respective S and V pixels are multiplied by the correction gain value (where the H pixel is not subjected to multiplication in this case), and at least two pixels are multiplied by the same correction gain value.

Structure of Second Embodiment

Figure 5:
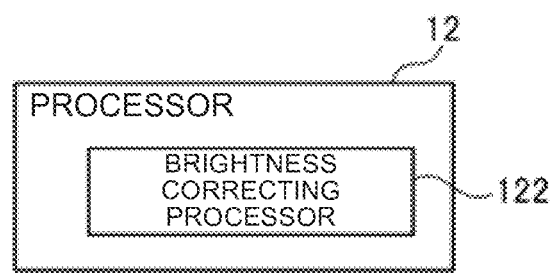
FIG. 5 is a block diagram illustrating a structure of a processor according to Embodiment 2.

Next, Embodiment 2 will be described. As illustrated in FIG. 5, the processor 12 according to Embodiment 2 includes a brightness correcting processor 122. The brightness correcting processor 122 performs the brightness correction, sets the peripheral part other than the center part that has a high probability as diseases in the picked-up image as the measuring area, creates the brightness histogram relative to the measuring area, calculates the correction gain value based on the peak value of the brightness histogram, and multiples the respective R, G, and B pixels by the same correction gain value so as not to change the color phase, thereby obtaining the corrected brightness value.

In this case, the brightness correcting processor 122 sets the center part as the center circle of the picked-up image, counts the number of pixels for each brightness value within the measuring area other than the center circle, obtains the addition-average relative to the adjacent brightness value to make the brightness histogram smooth in the brightness direction, obtains the peak value of the brightness histogram at the high brightness side, sets the target value for the brightness correction, calculates the correction gain that causes the peak value prior to the correction to be the target value, and multiplies the respective R, G, and B pixels by the obtained correction gain value, thereby performing the brightness correction.

The brightness correcting processor 122 may integrate the brightness histogram from the high brightness side to obtain the upper end value of the brightness, clip the correction gain value so that the upper end value does not exceed an upper limit, and obtain the eventual correction gain value.

Actions According to Second Embodiment

The brightness correcting process action by the processor 12 (brightness correcting processor 122) according to Embodiment 2 will be described with reference to the flowchart that is FIG. 6.

Under an instruction given by a medical doctor through the input device 30, first, when the dermoscopy imaging device 20 picks up an image of an affected area, the device main block 10 causes the picked-up image obtainer 11 to capture the picked-up dermoscopy image subjected to correction (step S701), and to output the captured image to the processor 12.

Figure 7:
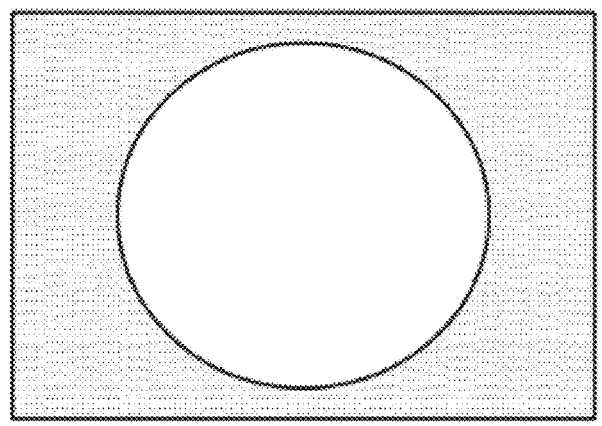
FIG. 7 is a diagram cited to describe a brightness information measuring area according to Embodiment 2.

In response to the output image, the processor 12 causes the brightness correcting processor 122 to set the brightness information measuring area (step S702). The brightness correcting processor 122 sets, for example, as illustrated in FIG. 7, the obtainment area other than the center circle area of the image (the peripheral part other than the center part) in order to obtain the brightness information on the image. The purpose of this action is to make a determination based on the brightness of the image with reference to the skin color, and to avoid the affected area that changes variously and is the center part of the image.

Figure 8:
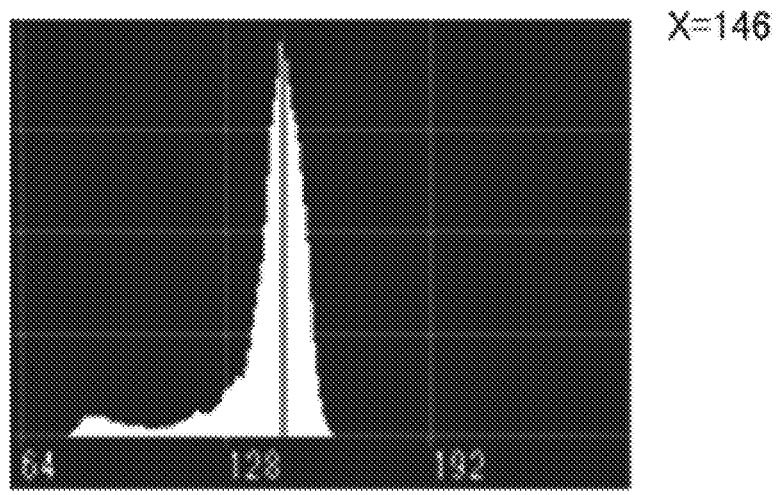
FIG. 8 is a diagram illustrating an example of a brightness histogram created according to Embodiment 2.

Next, the brightness correcting processor 122 creates the brightness histogram within the area (step S703). That is, the brightness correcting processor 122 counts the number of pixels for each brightness as for the brightness signals Y (0 to 255) within the area set in the step S702, and creates, for example, the histogram illustrated in FIG. 8.

Next, the brightness correcting processor 122 performs an addition averaging relative to the adjacent brightness value in order to stably obtain the peak value of the histogram, and performs a histogram smoothing process in the brightness direction by a low pass filter (LPF) (step S704). Subsequently, the brightness correcting processor 122 detects the peak value of the histogram at the high brightness side (step S705). For example, according to the brightness histogram illustrated in FIG. 8, X=146 is obtained as the peak value.

Figure 9:
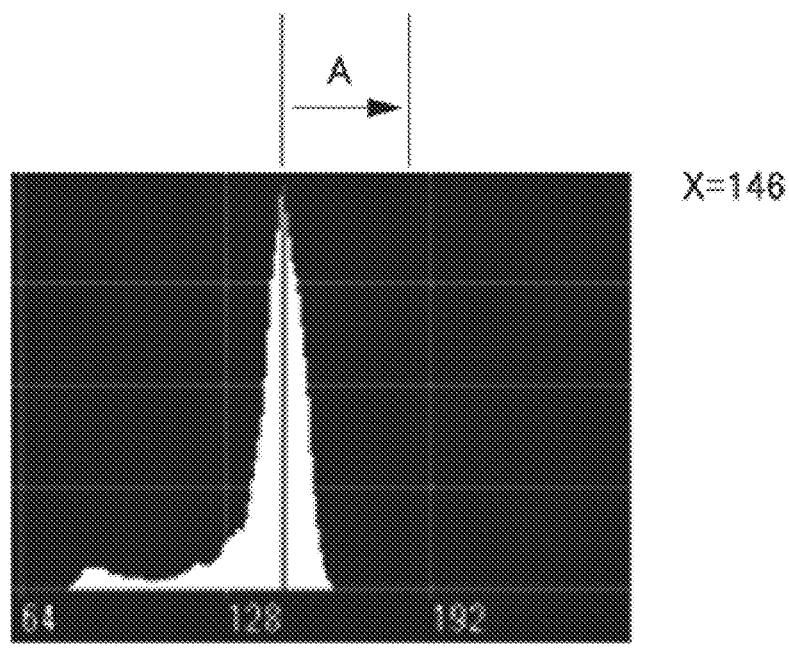
FIG. 9 is a diagram cited to describe a gain setting process according to Embodiment 2.

Next, the brightness correcting processor 122 executes a gain value calculating process that converts the peak value into the target value for the brightness correction (step S706). In this case, as is indicated by an arrow A in FIG. 9, the target value for the brightness correction is set to be 190, and the correction gain value that is 190/146 is calculated in such a way that the peak value 146 prior to the correction becomes 190.

Figure 10:
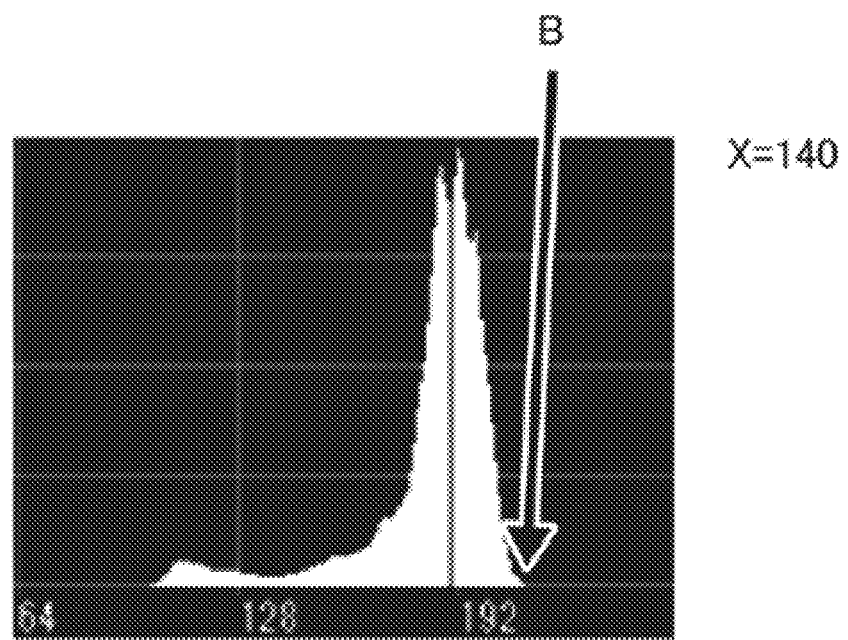
FIG. 10 is a diagram cited to describe a gain clipping process according to Embodiment 2.

Next, the brightness correcting processor 122 obtains the upper end value of the histogram in order to suppress the overexposure of some portions due to excessively increased correction gain. In this case, the upper end value of the brightness that becomes equal to or greater than 0.7% by integration on the histogram from the high brightness side (step S707). Subsequently, when the obtained upper end value exceeds 230, as is indicated by an arrow B in FIG. 10, the correction gain value is clipped that the upper end value does not exceed this value (step S708).

Figure 11:
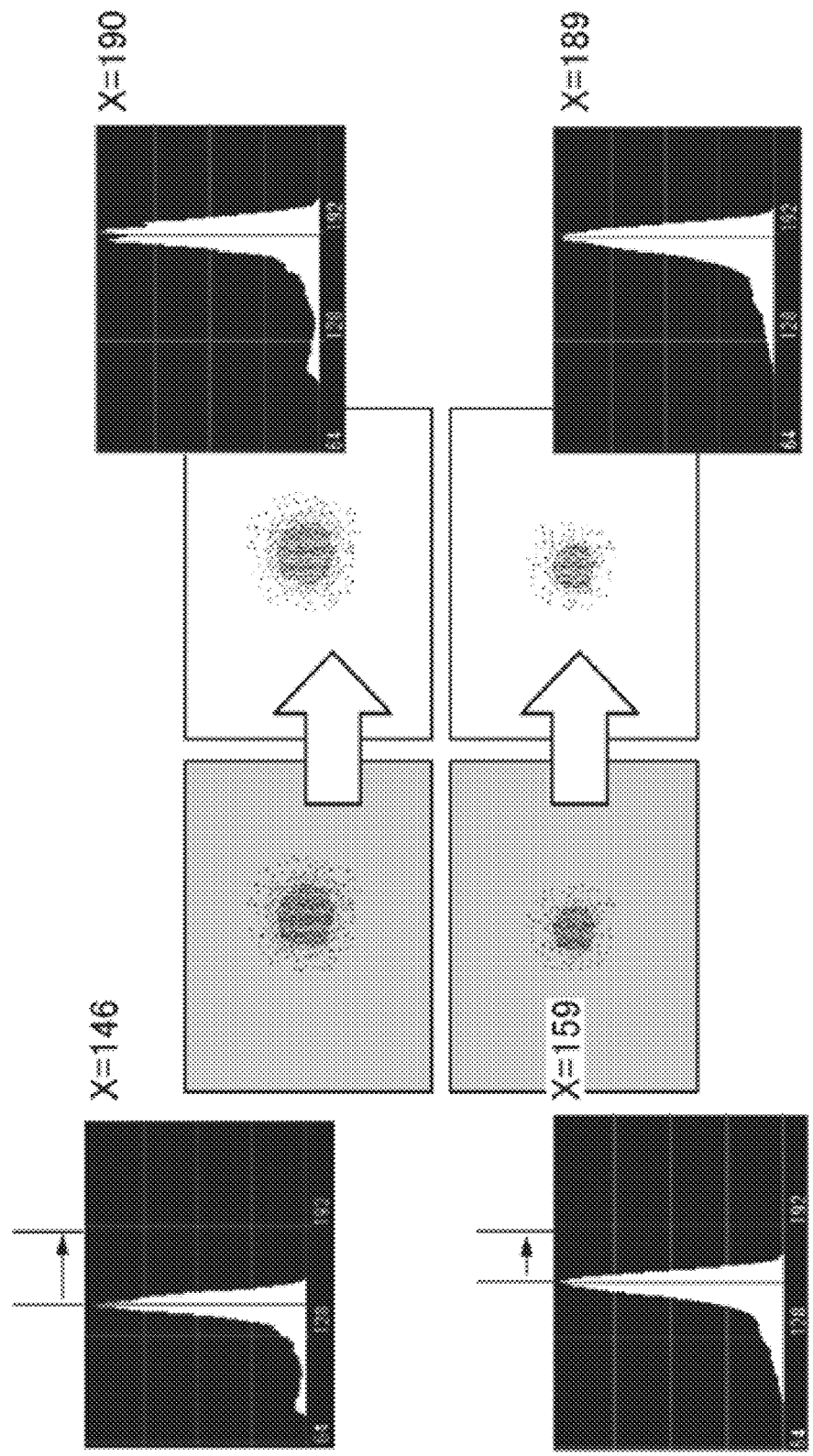
FIG. 11 is a diagram illustrating an example of an image before and after the brightness correction according to Embodiment 2.

Eventually, the brightness correcting processor 122 multiplies the respective R, G, and B pixels by the eventual correction gain value obtained in the step S708, thereby performing the brightness correction without changing a color phase (step S709), and ends the sequential brightness correcting process. FIG. 11 illustrates an example of the image before and after the brightness correction and that of each histogram before and after the brightness correction.

Effects of Second Embodiment

According to the diagnosis assisting device 1 of the above second embodiment, when the brightness correction is performed on the dermoscopy image subjected to the correction, the processor 12 (the brightness correcting processor 122) sets, as the brightness measuring area, the peripheral part other than the center part that has a high probability as the affected area, creates the brightness histogram for such an area, calculates the correction gain value based on the histogram peak value, and multiples the respective R, G, and B pixels by the same correction gain value, thereby performing a natural and robust brightness correction. When the brightness histogram is to be created, by limiting the creation target area to be only the area close to the skin color, the diagnosis precision further improves.

According to the diagnosis assisting device 1 of this embodiment, the determination on the skin color area is properly adopted to the dermoscopy image subjected to the correction, and a condition setting in view of space and a condition setting in view of the peak value of the histogram are made to execute the brightness correction. Hence, the result involves a characteristic process unique to the application. Hence, the adverse effect of the imaging light source and that of the individual difference of the melanin concentration can be eliminated, and a diagnosis assistance utilizable for the pre-process for image classification and the image presentation is enabled. This facilitates user to overview and grasp the difference of the affected area when multiple images are presented side by side, and consequently, a highly precise diagnosis assistance is enabled.

The image processing method according to this embodiment is, for example, as illustrated in FIG. 1, the image processing method in the diagnosis assisting device 1 that diagnose lesions from the picked-up image. This method includes (A) performing an image processing on the picked-up image, and in (A) performing the image processing, a peripheral area other than a center area that has a high probability as diseases in the picked-up image is set to be a measuring area when the image correction is performed.

Figure 3:
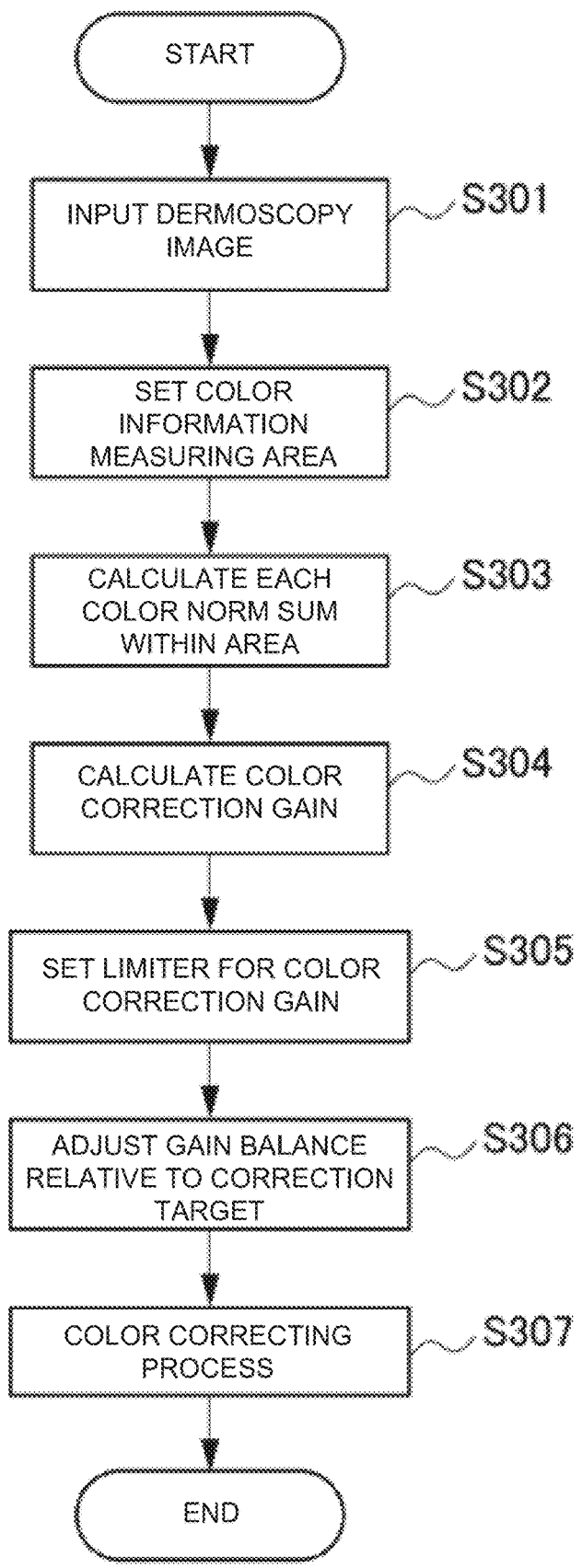
FIG. 3 is a flowchart illustrating a color correcting process action according to Embodiment 1.
Figure 6:
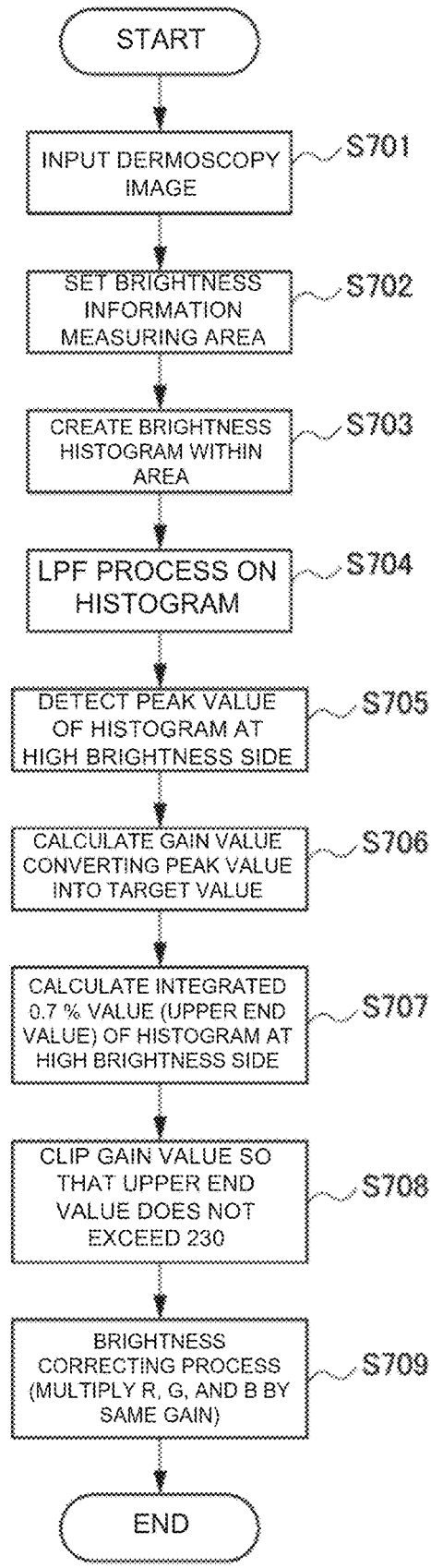
FIG. 6 is a flowchart illustrating a brightness correcting process action according to Embodiment 2.

In this case, the action (A) corresponds to, for example, procedures in the steps S301 to S307 of Embodiment 1 illustrated in FIG. 3, and the action (B) corresponds to, for example, procedures in the steps S701 to S709 of Embodiment 2 illustrated in FIG. 6.

In addition, according to the image processing method of this embodiment, the (A) performing the image processing may include (A1) setting the center part as a center circle of the picked-up image, (A2) obtaining an Lp norm of a corresponding pixel for each of R, G, and B within the measuring area other than the center circle, and normalizing by a coefficient k in such a way that an L2 norm of $e_R$, $e_G$ and $e_B$ becomes 1, (A3) a color gain is set using a product of ec times the square root of 3, and (A4) multiplying each pixel by a gain coefficient of R, G, and B to perform a color correcting process on an original image.

In this case, the action (A1) corresponds to the step S302 of Embodiment 1 illustrated in FIG. 1, the action (A2) corresponds to the step S303 of Embodiment 1 illustrated in FIG. 3, the action (A3) corresponds to the step S304 of Embodiment 1 illustrated in FIG. 3, and the action (A4) corresponds to the step S307, respectively.

Still further, according to the image processing method of this embodiment, the (A) performing the image processing may include (A11) setting the center part as a center circle of the picked-up image, (A12) counting a number of pixels for each brightness value within the measuring area other than the center circle to create the brightness histogram, (A13) taking an addition average relative to an adjacent brightness value to perform smoothing on the brightness histogram in a brightness direction, and obtaining the peak value of the brightness histogram at a high brightness side, (A14) setting a target value for a brightness correction, and setting the correction gain that causes the peak value prior to correction to be the target value, and (A15) multiplying each of R, G, and B by the obtained correction gain to perform a brightness correction.

In this case, the action (A11) corresponds to the steps S701 and S702 of Embodiment 2 illustrated in FIG. 6, the action (A12) corresponds to the steps S703 of Embodiment 2 illustrated in FIG. 6, the action (A13) corresponds to the steps S704 and S705 of Embodiment 2 illustrated in FIG. 6, and the action (A14) corresponds to the step S706 of Embodiment 2 illustrated in FIG. 6, and the action (A15) corresponds to the steps S707 to S709 of Embodiment 2 illustrated in FIG. 6, respectively.

According to the image processing method in this embodiment, the pre-process for image classification and the image presentation without an adverse effect of an imaging light source and that of the individual difference of melanin concentration are enabled. This facilitates to a user to, in particular, overview and grasp the difference of the affected area when multiple images are presented side by side. Consequently, a highly precise diagnosis assistance is enabled.

The method according to this embodiment is executable by a computer in the form of a program. This program is, for example, the program for the image processing method in the diagnosis assisting device 1 that diagnoses lesions from the picked-up images. This program causes the computer (device main block 10) to execute the similar processes to the actions in the above image processing method according to this embodiment. Hence, in order to avoid the redundancy, the descriptions of each action will not be repeated.

According to this program, the device main block 10 (processor 12) that reads and executes the above program enables the pre-process for image classification and the image presentation without an adverse effect of an imaging light source and that of the individual difference of melanin concentration. This facilitates a user to, in particular, overview and grasp the difference of the affected area when multiple images are presented side by side. Consequently, a highly precise diagnosis assistance is enabled. The program is stored in an unillustrated program memory in the device main block 10.

Structure According to Third Embodiment

Next, Embodiment 3 will be described. According to Embodiment 3, the dermoscopy image having undergone the color correcting process (normalization) according to Embodiment 1 and/or the brightness correcting process (normalization) according to Embodiment 2 is input to an identifier formed of a neural network, and unknown diseases to be surveyed is inferred based on the result of machine learning. In this case, after the color and/or brightness of the skin color part of the dermoscopy image is normalized, the target value for normalization is reduced, and then the dermoscopy image is input to the neural network.

Figure 12:
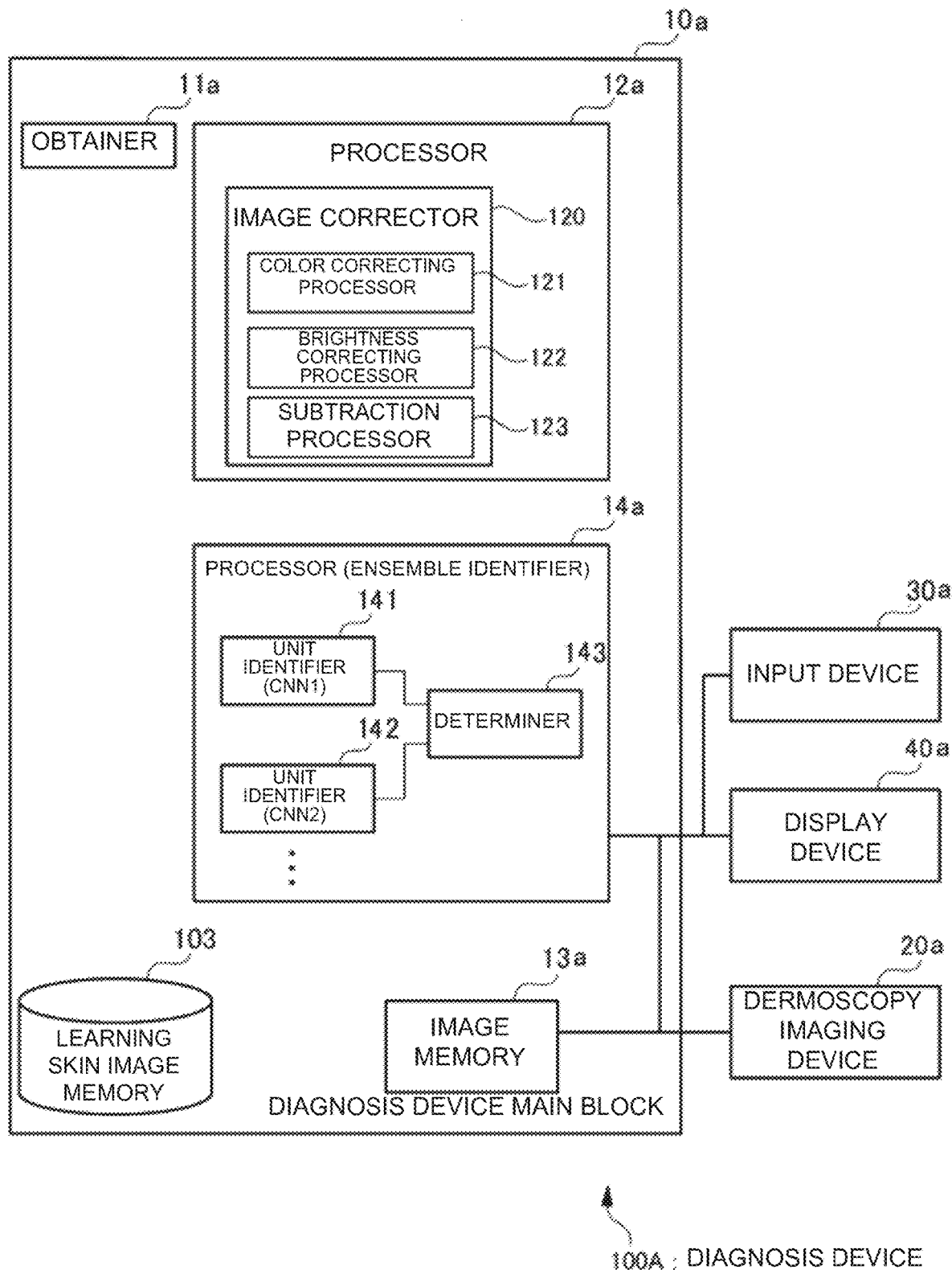
FIG. 12 is a block diagram illustrating a structure of a diagnosis assisting device according to Embodiment 3.

FIG. 12 is a block diagram illustrating a structure of a diagnosis device 100A according to Embodiment 3. As illustrated in FIG. 12, the diagnosis device 100A according to Embodiment 3 of the present disclosure is connected to a dermoscopy imaging device 20a.

The dermoscopy imaging device 20a picks up an image in accordance with an instruction from the diagnosis device 100A, stores the picked-up image (dermoscopy image) in an image memory 13a, and displays on a display device 40a. In addition, the picked-up image is subjected to the image processing by a diagnosis device main block 10a (a processor 12a, and an ensemble identifier 14a), and is stored in the image memory 13a, and also displayed on the display 40a.

An input device 30a is to instruct a start of a dermoscopy image pickup, and to select a part within the dermoscopy image to be described later, and the like. The display device 40a includes, for example, an LCD monitor, and the input device 30 includes a mouse, and the like.

A learning skin image memory 103 is a skin image database that stores a known skin image database in association with the identification name for diseases given for learning.

The diagnosis device main block 10a includes the processor 12a, the ensemble identifier 14a, and an obtainer 11a.

The processor 12a performs an image correcting process on the picked-up image (original image data) stored in the image memory 13a to create conversion image data, and outputs the conversion image data to the ensemble identifier 14a. In this case, the image correcting process is the color correcting process (normalization) of the original image data or the brightness correcting process (normalization) thereof. The converted image data may include a rotation and inversion image data that is the rotated or inverted conversion image data.

Hence, the image corrector 120 of the processor 12a includes the color correcting processor 121, the brightness correcting processor 122, and a subtraction processor 123.

The color correcting processor 121 sets, as the measuring area, the peripheral part other than the center part having a high probability as diseases in the picked-up image, and sets the correction conversion target to be the skin color for color correction, thereby performing the color correcting process. The brightness correcting processor 122 sets, as the measuring area, the peripheral part other than the center part that has a high probability as diseases in the picked-up image, creates the brightness histogram relative to the measuring area, calculates the correction gain value based on the peak value of the brightness histogram, and multiplies each of R, G, and B pixels by the correction gain value so as not to change the color phase, thereby obtaining the corrected brightness value. The color correcting processor 121 is the same as that of Embodiment 1, and the brightness correcting processor 122 is the same as that of Embodiment 2, and thus the detailed descriptions thereof will not be repeated.

The subtraction processor 123 subtracts a normalization target value from the pixel value of the dermoscopy image having undergone the color correcting process (normalization) and/or brightness correcting process (normalization) prior to an input to the ensemble identifier 14a (neural network). For example, the target values relating to the skin color part are set to be (R, G, B)=(200, 180, 200). This enables a pre-process of emphasizing a change in the skin color part (non-affected area) at the center part that has a possibility as diseases. That is, when the average image is subtracted, the value around the skin color does not always become center, but by subtracting the target value relating to the skin color part, a change in the skin color part (non-affected area) at the center part that has a possibility as diseases can be emphasized with the value around the skin color being as the center. When an emphasis to the change relative to the skin color part is unnecessary, as for the value to be subtracted, an average image value (average pixel value, for example, the pixel value of a gray color that will be a reference) instead of the target value (target pixel value) relating to the skin color part.

The dermoscopy image from which the normalization target value is subtracted is input to the ensemble identifier 14a. The ensemble identifier 14a identifies whether or not the input image indicates diseases based on multiple pieces of unknown skin image data relating to the object that is pre-processed by the processor 12a and is to be diagnosed. The ensemble identifier 14a includes at least two unit identifiers 141(CNN1) and 142(CNN2), so as to correspond to multiple pieces of the skin image data containing at least two of original image data relating to the object, the "first conversion image data" converted from the original image data, and the "second conversion image data" likewise converted from the original image data, and a determiner 143 integrating the identification values obtained by the respective unit identifiers 141, 142, and the like, and obtaining an eventual determination value.

The unit identifier 141, 142, and the like, includes a convolutional neural network (CNN) that performs learning based on the multiple pieces of known skin image data relating to diseases, and the learning is performed beforehand by inputting the conversion image data created by the processor 12a into this convolution neural network, and thus a function of an identifier that creates classification information enabling identification of diseases to be diagnosed is accomplished.

The unit identifiers 141, 142, and the like, may perform learning beforehand prior to the shipping of the diagnosis device 100A from a manufacturing factory, or may perform learning beforehand after the shipping and at a hospital, or the like. The term "beforehand" in this case means a time point prior to identification of diseases to be diagnosed.

Figure 13:
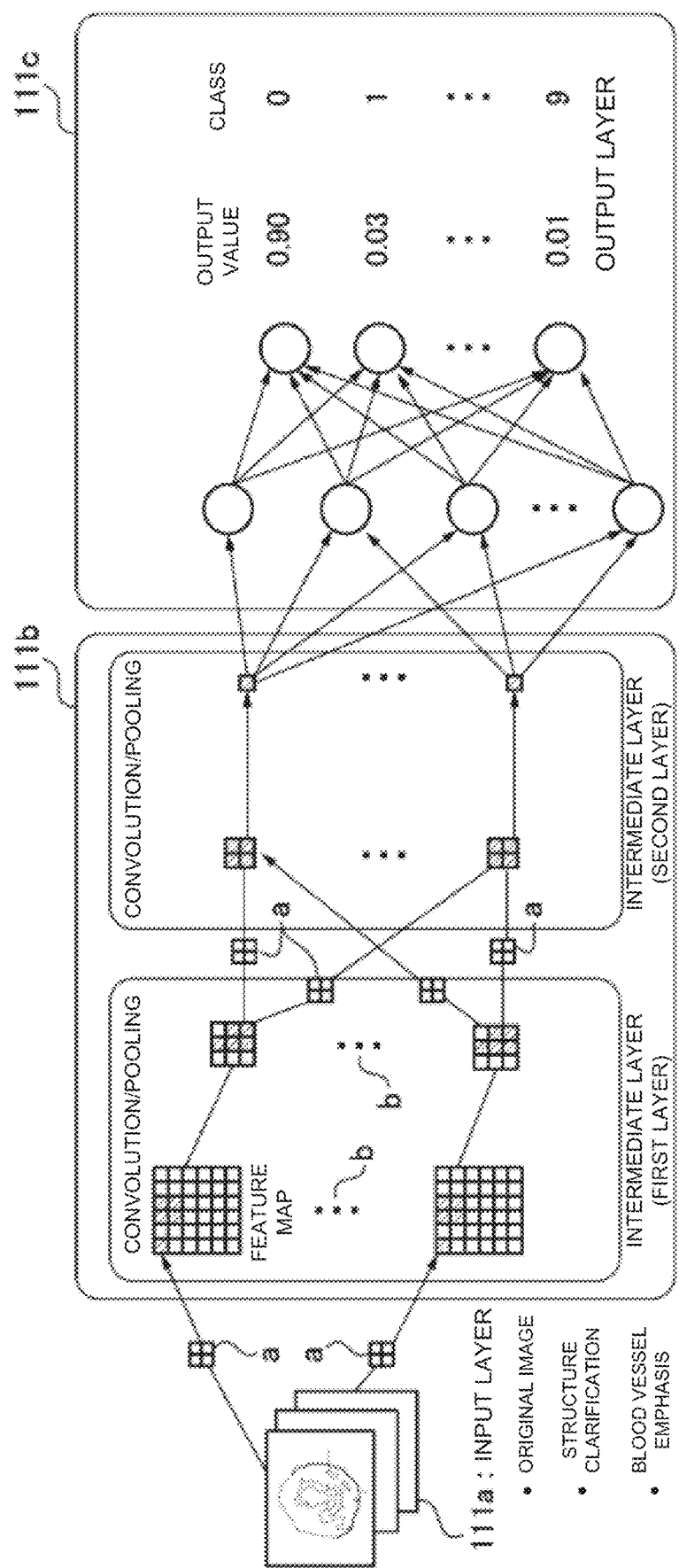
FIG. 13 is a block diagram illustrating a structure of an ensemble identifier (neural network) according Embodiment 3.

FIG. 13 illustrates a representative structure of a convolution neural network (CNN). In FIG. 13, the convolution neural network includes an input layer 111a into which multiple pieces of known skin image data (conversion image data) are input at the learning stage, and into which multiple pieces of unknown skin image data (conversion image data) are input at an check stage, an intermediate layer 111b that includes multiple sets of convolution layers and pooling layers, and extracts a feature from the multiple pieces of known skin image data or the multiple pieces of unknown skin image data, and an output layer 111c that outputs an identification value for each classification of the diagnosis object based on the extracted feature.

The process of the convolution neural network is executed via multiple process units a connected in a multi-stage manner. The input and output as for each process unit a are multiple two-dimensional image indicated by a feature map b that is multiple features extracted from the input image. In this case, the input image is regarded as a sheet of feature quantity map. In this case, a pair of convolution arithmetic processing unit and pooling unit is connected as the process unit a, and such multiple process units a are connected in a multi-stage manner Each process unit a calculates a feature quantity vector. The determiner 113 to be described later performs an identifying process on this feature quantity vector, and thus an output class is obtained.

The determiner 113 has the extracted feature input thereto, and identifies the feature. The learning by the convolution neural network updates the weighting of each layer by learning based on a backpropagation scheme. A multi-layer perceptron is applied as the identifying process. The multi-layer perceptron includes the input layer 111a, the intermediate layer 111b, and the output layer 111c. This is a non-linear class identifier. The weighting between the layers is obtained by stochastic gradient descent based on the backpropagation scheme. At the time of identification, the feature quantity is propagated in sequence, and the image is classified with the output by each unit of the output layer being as a post-probability of each class. In this case, the identification values obtained by the respective unit identifiers 141, 142, and the like, are integrated by, for example, averaging, so as to obtain the eventual determination value.

The convolution neural network is a general scheme to highly precisely classify images, and details are described at, for example, the Internet URL (http://en.wikipedia.org/wiki/Convolutional neural network). The convolution neural network (CNN) is a type of deep learning (deep neural network: DNN) that performs learning with a multi-layer structure of a neural network that simulates a brain neural circuit network, and is suitably applicable to image analysis. Other schemes than the deep learning are also applicable, and the deep learning may be combined with the other schemes.

The obtainer 12a is capable of obtaining multiple pieces of unknown skin image data, and outputs the skin image data to a pre-processor 10a for the purpose of image conversion like structure clarification, partial emphasis, and the like.

Actions According to Third Embodiment

The action of the processor 12a and that of the ensemble identifier 14a according to Embodiment 3 will be described in detail with reference to the flowcharts that are FIGS. 14 to 18.

Figure 14:
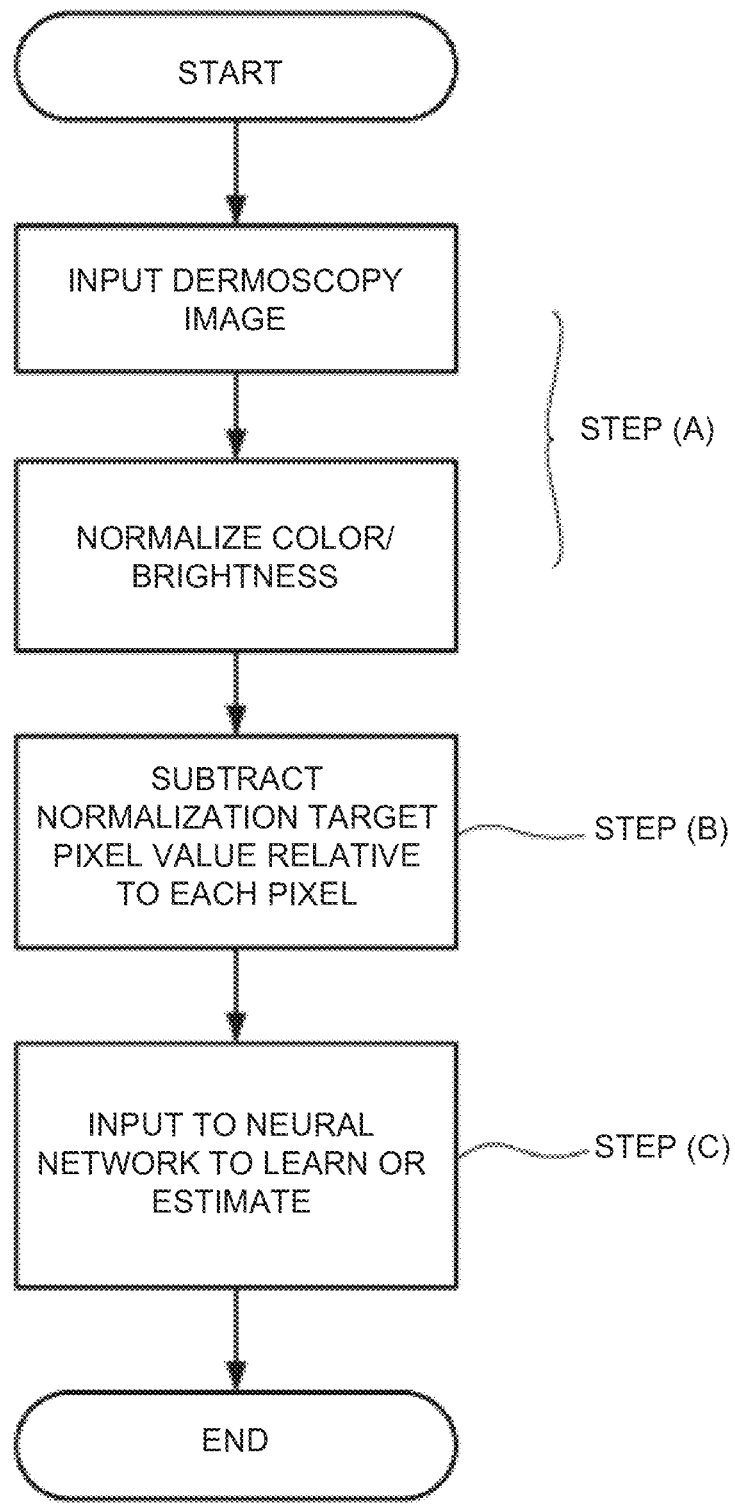
FIG. 14 is a flowchart illustrating a basic action of the diagnosis assisting device according to Embodiment 3.
Figure 15:
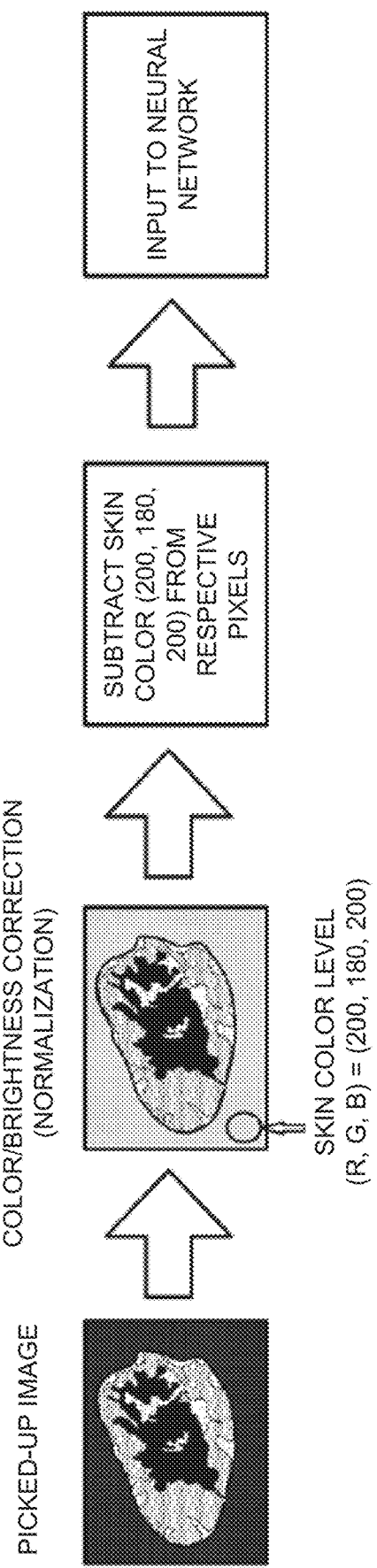
FIG. 15 is a diagram to complementary describe the flowchart that is FIG. 14.

First, as illustrated in FIG. 14, a desired picked-up dermoscopy image is input, and the color correcting process (normalization) according to Embodiment 1 and/or the brightness correcting process (normalization) according to Embodiment 2 is performed on the dermoscopy image (step (A)). The color and/or brightness correcting process (normalization) sets, as illustrated in FIG. 15, the normalization target values to be, for example, (R, G, B)=(200, 180, 200). By this normalization, the skin color part (non-affected area) is corrected to an image close to the skin color from the bluish picked-up image. The details of the step (A) are as described together with the steps S301 to S307 illustrated in FIG. 3 for the color correcting process, and the steps S701 to S709 illustrated in FIG. 6 for the brightness correcting process.

Returning to FIG. 14, the target values (R, G, B)=(200, 180, 200) relating to the skin color are subtracted from the respective pixels of the image having undergone the normalization (step (B)). This subtraction enables the pre-process of emphasizing the change relative to the skin color part (non-affected area) that has a possibility as diseases as described above.

The image having undergone the subtraction is input to the ensemble identifier 14a comprising the neural network to perform learning or estimation (step (C)). The details of the learning and estimation by the identifier will be described later. The step (C) can be performed prior to the step (B), and prior to the subtraction of the target values, each pixel of the image having undergone the normalization may be input to the ensemble identifier 14a for learning or estimation.

Actions According to Third Embodiment

The actions of the diagnosis device 100A according to Embodiment 3 of the present disclosure will be described in detail with reference to the flowcharts that are FIGS. 16 to 18. The following actions can be constructed as a learning process program to be executed by a computer.

Figure 16:
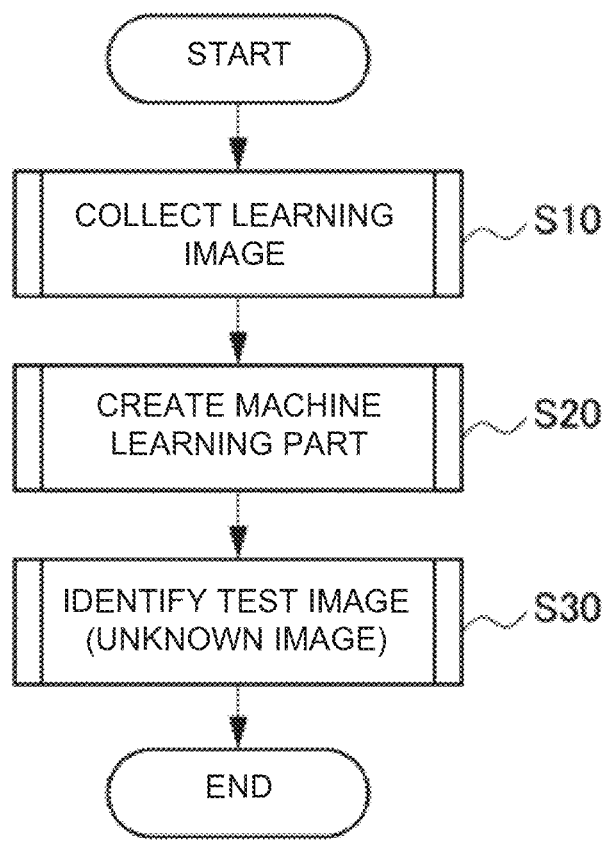
FIG. 16 is a flowchart illustrating a basic action of the ensemble identifier according to Embodiment 3.

In FIG. 16 (and also FIG. 13 as needed), first, the obtainer 11a of the diagnosis device main block 10 obtains multiple pieces of unknown skin image data relating to the diagnosis object as learning skin image data (step S10: collect learning image). More specifically, as for the collection of the unknown skin image data, when a medical doctor performs dermoscopy imaging on the affected area of a patient, the obtainer 11a captures the multiple pieces of unknown skin image data by the imaging operation, and outputs the captured image to the processor 12a.

At this time, the processor 12a registers the disease name of the case in the learning skin image memory 103 in association with the collected learning skin image data. Next, the processor 12a determines whether or not the necessary number of learning skin images is collected, repeatedly executes the above procedures until the necessary number of images is collected, and constructs a skin image database on the learning skin image memory 103.

After the obtainer 11a executes the unknown skin image data collecting process in the step S10, the processor 12a performs the image conversion process on the unknown image data, such as structure clarification, partial emphasis, and the like, further performs a data increasing process like rotation by 90 degrees, and outputs the image data to the ensemble identifier 14a. The ensemble identifier 14a extracts the feature of the learning skin image that is the input image by the unit identifiers 141, 142, and the like, that repeatedly execute convolution arithmetic processing and pooling by a weighting filter (step S20: machine learning part creating process).

More specifically, the unit identifiers 141, 142, and the like, perform raster scanning on the input image using the weighting filter to repeatedly execute convolution arithmetic processing, thereby obtaining the feature map b. Subsequently, the unit identifiers 141, 142, and the like, perform pooling on the feature quantity map b, and perform the identifier creating process of outputting a value from a small area of the (m−1)th feature quantity map b that is m−1, and converting into (m)th feature quantity map.

Next, the determiner 143 has the features extracted by the unit identifiers 141, 142, and the like, and input to this determiner to perform identification. A multi-layer perceptron is applied as the identifying process, and at the time of identification, the feature quantity is propagated in sequence, and the input image is classified with the output by each unit in the output layer 11c being as the posterior probability of each class, and thus the identifying process is performed on the unknown image (step S30: diagnosis image identification).

Figure 17:
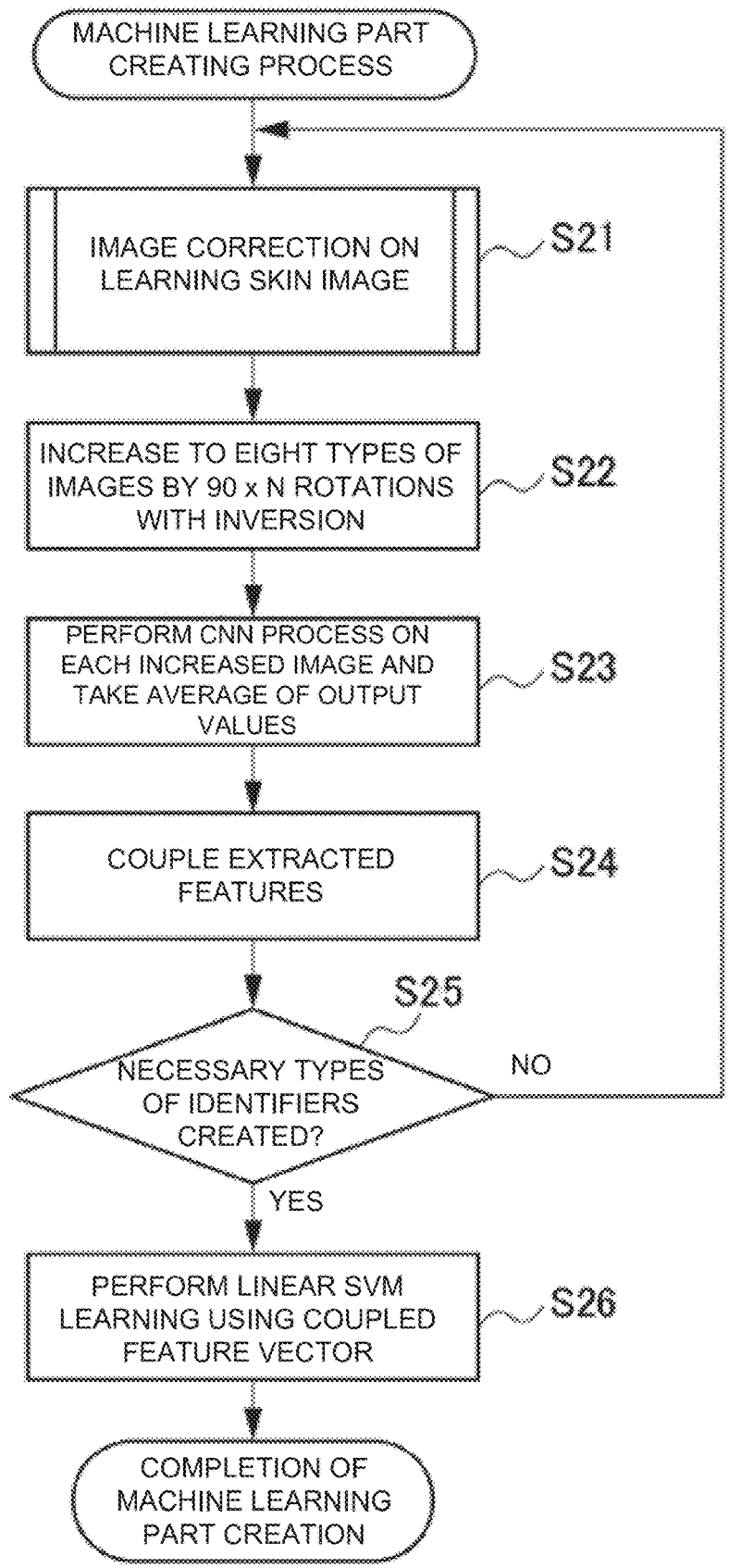
FIG. 17 is a flowchart illustrating a flow of a machine learning part creating process according to Embodiment 3.

FIG. 17 is a flowchart illustrating procedures (step S20 in FIG. 16) of the machine learning part creating process by the diagnosis device 100A according to Embodiment 3 of the present disclosure. First, the processor 12a performs the image correcting process on the learning skin image that is the color correction (normalization) and/or brightness correction (normalization) (step S21). Next, a process of increasing each conversion image to be eightfold that is a combination of 90×N rotations with inversion is performed, and the process result is given to the ensemble identifier 14a (step S22).

In response to the given result, the ensemble identifier 14a takes an average of learnt CNN values of the respective increased images for each conversion image to obtain 4096-dimensional feature vector (step S23). The ensemble identifier 14a further couples the feature vector averages output conversion image by conversion image to obtain an eventual vector expression (step S24). The processes from the step S21 to the step S24 are repeatedly executed to create the necessary types of identifiers (step S25: YES), performs a linear support vector machine (SVM) learning using the coupled feature vector as an input, and ends the machine learning part creating process (step S26).

FIG. 18 is a flowchart illustrating procedures (step S30 in FIG. 16) of the diagnosis image identifying process by the diagnosis device 100A according to Embodiment 3 of the present disclosure. As illustrated in FIG. 18, first, the processor 12a executes the image correcting process on the unknown skin image obtained by the obtainer 11a for the color correction (normalization) and/or the brightness correction (normalization) (step S31). The processor 12a further executes the increasing process on each conversion image to be eightfold by a combination of 90×N rotations with inversion, and the process result is given to the ensemble identifier 14a.

The ensemble identifier 14a takes an average of learnt CNN values of the respective increased images for each conversion image to obtain 4096-dimensional feature vector, and further couples the feature vector averages output conversion image by conversion image to obtain an eventual vector expression (step S32). Next, the ensemble identifier 14a repeatedly executes the processes in the step S31 and in the step S32 to create the necessary types of identifiers (step S33: YES), and the determiner 113 takes an average of all identification values to obtain an eventual determination value, and for example, displays on the display device 40a (step S34).

That is, according to the processes from the step S31 to the step S33, the input image subjected to the image conversion is simply changed from the learning skin image to the test image (unknown image), and after the necessary types of identifiers are created, the identification result is obtained based on the output value by the learnt linear SVM identifier.

Effects of Third Embodiment

According to the diagnosis assisting device 1 of Embodiment 3, the color and/or brightness of the skin color part (non-affected area) of the dermoscopy image is normalized, and by performing the subtraction as the pre-process with the normalization value, the pre-process of emphasizing the change relative to the skin color part (non-affected area) of the center part that has a possibility as diseases can be performed. In other words, an effective edge extraction relative to the center part and the skin color part (non-affected area) is enabled.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled. More specifically, the above embodiments have been described for an example case in which skin lesions are observed, but the present disclosure is applicable to lesions other than skin, such as an eyeground and organs like uterus.

What is claimed is:

1. An image processing method in a diagnosis assisting device that diagnoses lesions from a picked-up image, the method comprising:
A) performing an image correction on the picked-up image for diagnosis, and B) obtaining an input image to an identifier that identifies diseases based on the picked-up image having undergone the image correction, wherein:

performing the image correction in A) comprises performing a brightness correction, and performing the brightness correction comprises:

setting a peripheral area other than a diagnosis area in the picked-up image as a measuring area, creating a brightness histogram relative to the measuring area, calculating a correction gain value based on a maximum peak value of the created brightness histogram, wherein calculating the correction gain value comprises integrating the brightness histogram from the maximum peak value toward a high brightness side, obtaining an upper end value of a brightness by calculating a predetermined percentage by integration on the brightness histogram from the maximum peak value toward the high brightness side, and clipping the correction gain value so that the upper end value does not exceed a predetermined upper limit, and correcting each of pixels in a color space by using the calculated correction gain value.

2. The image processing method according to claim 1, wherein:

in A), correcting each of the pixels in the color space comprises multiplying at least two pixels among the pixels in the color space by the same correction gain value so as not to change a color phase, to thereby obtain a corrected pixel value, and in B), an average pixel value of the picked-up image is subtracted from a pixel value of the picked-up image having undergone the image correction to obtain the input image to the identifier.

3. The image processing method according to claim 1, wherein in A), correcting each of the pixels in the color space comprises multiplying at least two pixels among the pixels in the color space by the same correction gain value to obtain a corrected pixel value.

4. The image processing method according to claim 1, wherein:

in A), performing the brightness correction comprises:

setting a center circle of the picked-up image as the diagnosis area, counting a number of pixels within the measuring area other than the center circle for each brightness value to create the brightness histogram, performing an addition average relative to an adjacent brightness value to perform smoothing on the brightness histogram in a brightness direction, obtaining the maximum peak value of the brightness histogram, setting a target value for the brightness correction, calculating, as the correction gain value, a correction gain value that causes the maximum peak value prior to the correction to become the target value of the brightness correction, the calculated correction gain value being clipped so that the upper end value does not exceed the predetermined upper limit, and multiplying each pixel by the calculated correction gain value to perform the brightness correction, and in B), a target pixel value of the brightness correction of the picked-up image is subtracted from a pixel value of the picked-up image having undergone the image correction to obtain the input image to the identifier.

5. The image processing method according to claim 1, wherein:

the color space includes at least one of an RGB color space, a YUV color space, or an HSV color space, and the pixels R, G, and B are multiplied by the same correction gain value in a case of the RGB color space, the pixels Y, U, and V are multiplied by the same correction gain value in a case of the YUV color space, and the pixels S and V are multiplied by the same correction gain value in a case of the HSV color space to obtain a corrected pixel value.

* * * * *